(12) United States Patent
Borza et al.

(10) Patent No.: US 12,168,007 B1
(45) Date of Patent: Dec. 17, 2024

(54) SUBSTITUTED PIPERAZINES AS DOPAMINE D3/D2 RECEPTOR MODULATORS

(71) Applicant: Richter Gedeon Nyrt, Budapest (HU)

(72) Inventors: István Borza, Budapest (HU); János Eles, Budapest (HU); Bálint Menczinger, Budapest (HU); Szilvia Bodnárné Deák, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 0 days.

(21) Appl. No.: 18/409,478

(22) Filed: Jan. 10, 2024

Related U.S. Application Data

(60) Provisional application No. 63/479,530, filed on Jan. 11, 2023.

(51) Int. Cl.
C07D 241/04 (2006.01)
A61K 31/495 (2006.01)
A61P 25/18 (2006.01)

(52) U.S. Cl.
CPC ............ A61K 31/495 (2013.01); A61P 25/18 (2018.01)

(58) Field of Classification Search
CPC .................................................. C07D 241/04
USPC ........................................... 544/395
See application file for complete search history.

(56) References Cited

U.S. PATENT DOCUMENTS

2023/0076435 A1   3/2023   Su et al.

FOREIGN PATENT DOCUMENTS

| EP | 4056568 A1 | 9/2022 |
| WO | WO-2005/012266 A1 | 2/2005 |
| WO | WO-2007/148208 A2 | 12/2007 |
| WO | WO-2010/151711 A1 | 12/2010 |
| WO | WO-2020/156312 A1 | 8/2020 |
| WO | WO-2021/083246 A1 | 5/2021 |
| WO | WO-2021/088920 A1 | 5/2021 |

OTHER PUBLICATIONS

Extended European Search Report for EP Application No. 24151077.5 dated Jun. 17, 2024.

Primary Examiner — Douglas M Willis
(74) Attorney, Agent, or Firm — Foley Hoag LLP; Hathaway P. Russell; Tracy L. Vrablik

(57) ABSTRACT

The present disclosure provides for compounds of Formula (I):

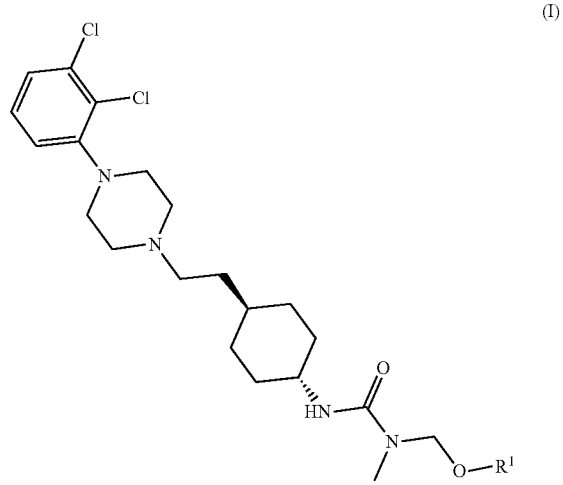

wherein $R^1$ has any of the values defined in the specification, and pharmaceutically acceptable salts thereof, that are useful as agents in the treatment of diseases and conditions including schizophrenia. Also provided are pharmaceutical compositions comprising compounds of Formula (I).

3 Claims, No Drawings

SUBSTITUTED PIPERAZINES AS DOPAMINE D3/D2 RECEPTOR MODULATORS

CROSS-REFERENCE TO RELATED APPLICATIONS

The instant application claims the benefit of U.S. Provisional Patent Application Ser. No. 63/479,530, filed Jan. 11, 2023, the content of which is incorporated by reference herein in its entirety.

FIELD

The present disclosure pertains to compounds which modulate the activity of the dopamine D2 and D3 receptors, methods of making such compounds, compositions containing the compounds, and methods of treatment using the compounds.

BACKGROUND

Dysfunction of the dopaminergic neurotransmitter system can be observed in the pathology of neuropsychiatric disorders including schizophrenia and emotional or cognitive dysfunctions (Sokoloff, P. et al: Nature, 1990, 347. 146; Schwartz, J.-C. et al.: Clin. Neuropharmacology., 1993, 16, 295). The effect of dopamine is mediated via at least five distinct dopamine receptors belonging to the dopamine D1 (i.e., D1 and D5), or D2 (i.e., D2, D3, and D4) receptor families. D3 receptors have characteristic distribution in the central dopaminergic systems. The dopamine D2 receptors are widely distributed in the brain and are involved in numerous physiological functions and pathological states. Dopamine D2 antagonists are used, for example, as antipsychotic agents. However, massive antagonism of the D2 receptors leads to unwanted side effects, such as extrapyramidal motor symptoms, psychomotor sedation, or cognitive blunting. Antipsychotic agents preferentially targeting of the D3 receptors provide successful therapeutic intervention in the treatment of schizophrenia.

There remains a need in the art for improved compounds with D3/D2 receptor selectivity.

SUMMARY

In some embodiments, the disclosure provides for compounds of Formula (I), or a pharmaceutically acceptable salt thereof,

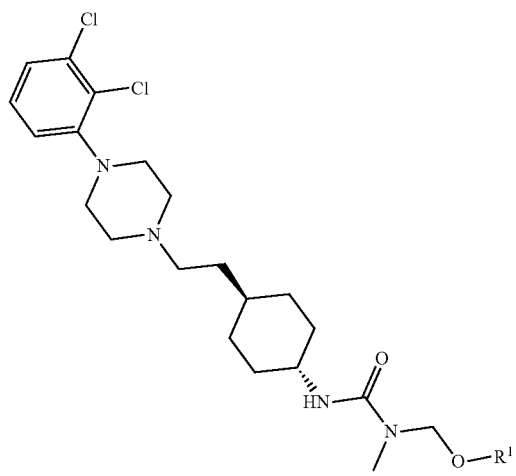

(I)

wherein
$R^1$ is $C_1$-$C_3$ alkyl.

In some embodiments, the disclosure provides for compounds of Formula (I), or a pharmaceutically acceptable salt thereof, wherein $R^1$ is $CH_3$.

In some embodiments, the disclosure provides for compounds of Formula (I), or a pharmaceutically acceptable salt thereof, wherein $R^1$ is $CH_2CH_3$.

In some embodiments, the disclosure provides for compounds of Formula (I), or a pharmaceutically acceptable salt thereof, wherein $R^1$ is $CH_2CH_2CH_3$.

In some embodiments, the disclosure provides compounds of Formula (I), wherein the compound is selected from the group consisting of:
N'-[(1r,4r)-4-{2-[4-(2,3-dichlorophenyl)piperazin-1-yl]ethyl}cyclohexyl]-N-(ethoxymethyl)-N-methylurea;
N'-[(1r,4r)-4-{2-[4-(2,3-dichlorophenyl)piperazin-1-yl]ethyl}cyclohexyl]-N-(methoxymethyl)-N-methylurea; and
N'-[(1r,4r)-4-{2-[4-(2,3-dichlorophenyl)piperazin-1-yl]ethyl}cyclohexyl]-N-methyl-N-(propoxymethyl)urea; or a pharmaceutically acceptable salt thereof.

In some embodiments, the disclosure provides a compound of Formula (I), wherein the compound is N'-[(1r,4r)-4-{2-[4-(2,3-dichlorophenyl)piperazin-1-yl]ethyl}cyclohexyl]-N-(ethoxymethyl)-N-methylurea; or a pharmaceutically acceptable salt thereof.

In some embodiments, the disclosure provides a compound of Formula (I), wherein the compound is N'-[(1r,4r)-4-{2-[4-(2,3-dichlorophenyl)piperazin-1-yl]ethyl}cyclohexyl]-N-(ethoxymethyl)-N-methylurea.

In some embodiments, the disclosure provides a compound of Formula (I), wherein the compound is a pharmaceutically acceptable salt N'-[(1r,4r)-4-{2-[4-(2,3-dichlorophenyl)piperazin-1-yl]ethyl}cyclohexyl]-N-(ethoxymethyl)-N-methylurea.

In some embodiments, the disclosure provides a pharmaceutical composition comprising a therapeutically effective amount of a compound of Formula (I), or a pharmaceutically acceptable salt thereof, in combination with a pharmaceutically acceptable carrier.

In some embodiments, the disclosure provides a method for treating schizophrenia, the method comprising the step of administering to the subject a therapeutically effective amount of a compound of Formula (I), or a pharmaceutically acceptable salt thereof.

In some embodiments, the disclosure provides a compound of Formula (I), or a pharmaceutically acceptable salt thereof, for use as a medicament.

In some embodiments, the disclosure provides a compound of Formula (I), or a pharmaceutically acceptable salt thereof, for use in the treatment of schizophrenia.

In some embodiments, the disclosure provides the use of a compound of Formula (I), or a pharmaceutically acceptable salt thereof, for the manufacture of a medicament for the treatment of schizophrenia.

DETAILED DESCRIPTION

The present disclosure describes compounds which modulate the activity of dopamine D3 and dopamine D2 receptors.

Compounds disclosed herein may contain one or more variable(s) that occur more than one time in any substituent or in the Formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

Certain terms as used in the specification are intended to refer to the following definitions, as detailed below.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds. Reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "$C_1$-$C_3$ alkyl," as used herein, refers to a saturated hydrocarbon chain radical having one, two, or three carbons unless otherwise specified. Representative examples of $C_1$-$C_3$ alkyl include methyl, ethyl, and n-propyl.

In some instances, the number of carbon atoms in a moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms.

The phrase "pharmaceutical composition" refers to a composition suitable for administration in medical use.

The phrase "pharmaceutically acceptable salt" refers to those salts which are, within the scope of sound medical judgement, suitable for use in contact with the tissues of humans and lower animals without undue toxicity, irritation, allergic response and the like and are commensurate with a reasonable benefit/risk ratio.

The term "stable" refers to compounds that possess stability sufficient to allow manufacture and that maintain the integrity of the compound for a sufficient period of time to be useful for the purpose detailed herein.

The phrase "therapeutically effective amount" refers to an amount of a compound, or a pharmaceutically acceptable salt thereof, sufficient to prevent the development of or to alleviate to some extent one or more of the symptoms of the condition or disorder being treated when administered for treatment in a particular subject or subject population.

The terms "treat," "treating," and "treatment," as used herein, refer to a method of alleviating or abrogating a disease and/or its attendant symptoms.

Compounds

Compounds of the present disclosure have the general Formula (I) as described herein.

In some embodiments, the present disclosure provides for compounds of Formula (I), or a pharmaceutically acceptable salt thereof,

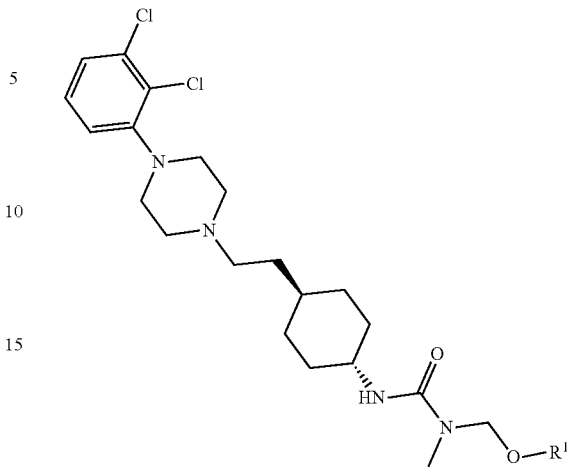

wherein
$R^1$ is $C_1$-$C_3$ alkyl.

In some embodiments, the present disclosure provides for compounds of Formula (I), or a pharmaceutically acceptable salt thereof, wherein $R^1$ is $C_1$ alkyl.

In some embodiments, the present disclosure provides for compounds of Formula (I), or a pharmaceutically acceptable salt thereof, wherein $R^1$ is $C_2$ alkyl.

In some embodiments, the present disclosure provides for compounds of Formula (I), or a pharmaceutically acceptable salt thereof, wherein $R^1$ is $C_3$ alkyl.

In some embodiments, the present disclosure provides for compounds of Formula (I), or a pharmaceutically acceptable salt thereof, wherein $R^1$ is selected from the group consisting of $CH_3$, $CH_2CH_3$, and $CH_2CH_2CH_3$.

In some embodiments, the present disclosure provides for compounds of Formula (I), or a pharmaceutically acceptable salt thereof, wherein $R^1$ is $CH_3$.

In some embodiments, the present disclosure provides for compounds of Formula (I), or a pharmaceutically acceptable salt thereof, wherein $R^1$ is $CH_2CH_3$.

In some embodiments, the present disclosure provides for compounds of Formula (I), or a pharmaceutically acceptable salt thereof, wherein $R^1$ is $CH_2CH_2CH_3$.

In some embodiments, the present disclosure provides a compound of Formula (I), wherein the compound is N'-[(1r,4r)-4-{2-[4-(2,3-dichlorophenyl)piperazin-1-yl]ethyl}cyclohexyl]-N-(ethoxymethyl)-N-methylurea; or a pharmaceutically acceptable salt thereof.

In some embodiments, the present disclosure provides a compound of Formula (I), wherein the compound is N'-[(1r,4r)-4-{2-[4-(2,3-dichlorophenyl)piperazin-1-yl]ethyl}cyclohexyl]-N-(ethoxymethyl)-N-methylurea.

In some embodiments, the present disclosure provides a compound of Formula (I), wherein the compound is a pharmaceutically acceptable salt of N'-[(1r,4r)-4-{2-[4-(2,3-dichlorophenyl)piperazin-1-yl]ethyl}cyclohexyl]-N-(ethoxymethyl)-N-methylurea.

In some embodiments, the present disclosure provides a compound of Formula (I), wherein the compound is N'-[(1r,4r)-4-{2-[4-(2,3-dichlorophenyl)piperazin-1-yl]ethyl}cyclohexyl]-N-(methoxymethyl)-N-methylurea; or a pharmaceutically acceptable salt thereof.

In some embodiments, the present disclosure provides a compound of Formula (I), wherein the compound is N'-[(1r, 4r)-4-{2-[4-(2,3-dichlorophenyl)piperazin-1-yl]ethyl}cyclohexyl]-N-(methoxymethyl)-N-methylurea.

In some embodiments, the present disclosure provides a compound of Formula (I), wherein the compound is a pharmaceutically acceptable salt of N'-[(1r,4r)-4-{2-[4-(2,3-dichlorophenyl)piperazin-1-yl]ethyl}cyclohexyl]-N-(methoxymethyl)-N-methylurea.

In some embodiments, the present disclosure provides a compound of Formula (I), wherein the compound is N'-[(1r,4r)-4-{2-[4-(2,3-dichlorophenyl)piperazin-1-yl]ethyl}cyclohexyl]-N-methyl-N-(propoxymethyl)urea; or a pharmaceutically acceptable salt thereof.

In some embodiments, the present disclosure provides a compound of Formula (I), wherein the compound is N'-[(1r,4r)-4-{2-[4-(2,3-dichlorophenyl)piperazin-1-yl]ethyl}cyclohexyl]-N-methyl-N-(propoxymethyl)urea.

In some embodiments, the present disclosure provides a compound of Formula (I), wherein the compound is a pharmaceutically acceptable salt of N'-[(1r,4r)-4-{2-[4-(2,3-dichlorophenyl)piperazin-1-yl]ethyl}cyclohexyl]-N-methyl-N-(propoxymethyl)urea.

Compounds of the present disclosure and intermediates were named by using ACD/Name 2021.1.3 (File Version N15E41, Build 123232, 7 Jul. 2021) software program and/or by using Struct=Name naming algorithm as part of CHEMDRAW® Professional v. 20.1.1.125.

Exemplary compounds of Formula (I) include, but are not limited to, the compounds shown in Table 1 below, and pharmaceutically acceptable salts thereof.

TABLE 1

Example 1

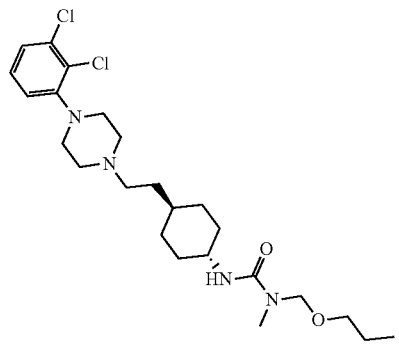

Example 2

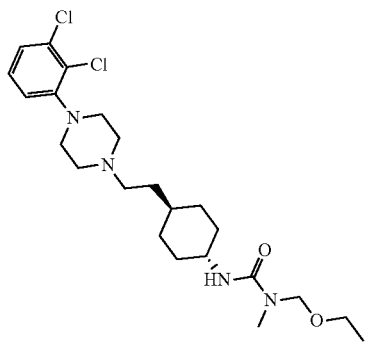 [SMILES: CCOCN(C)C(=O)N[C@H]1CC[C@H](CCN2CCN(c3cccc(Cl)c3Cl)CC2)CC1]

TABLE 1-continued

Example 3

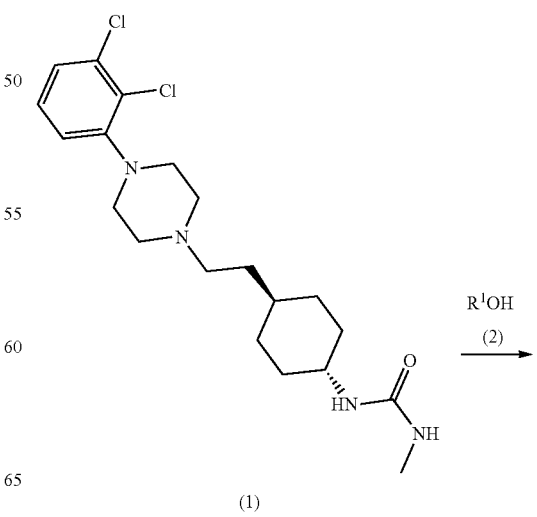

Compounds of Formula (I) may be used in the form of pharmaceutically acceptable salts. Compounds of Formula (I) may contain either a basic or an acidic functionality, or both, and may be converted to a pharmaceutically acceptable salt, when desired, by using a suitable acid or base.

Methods of Making Exemplary Compounds

The compounds of the present disclosure may be better understood in connection with the following synthetic schemes and methods which illustrate a means by which the compounds can be prepared. The compounds of the present disclosure can be prepared by a variety of synthetic procedures. Representative synthetic procedures are shown in, but not limited to, Schemes 1-2. The variable $R^1$ is defined as detailed herein, e.g., in the Summary.

Schemes

Scheme 1

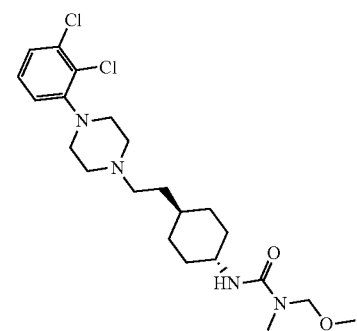 [SMILES: COCN(C)C(=O)N[C@H]1CC[C@H](CCN2CCN(c3cccc(Cl)c3Cl)CC2)CC1]

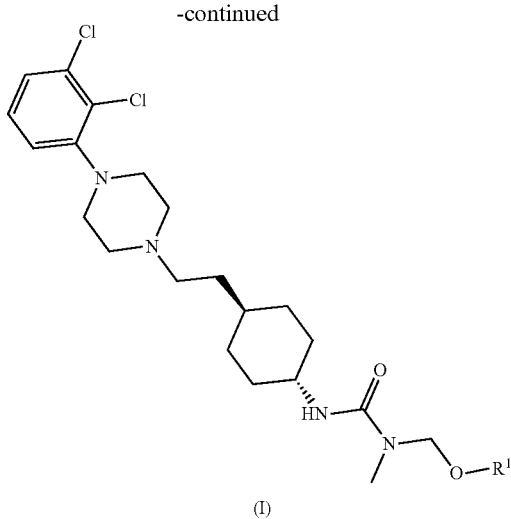

(I)

As shown in Scheme 1, compounds of formula (I), wherein R¹ is as defined herein, can be prepared from the compound of formula (1) which can be prepared according to methods known in the art, such as e.g. WO 2010/070370 A1. Accordingly, the compound of formula (1) can be treated with commercially available paraformaldehyde or formaldehyde (saturated aqueous solution with methanol stabilizer) and with the appropriate alcohol of formula (2), wherein R¹ is as described herein and which are either commercially available or can be prepared according to methods known in the art, at ambient temperature to reflux. The reaction is typically conducted for 1 to 168 hours in a suitable solvent such as, but not limited to, the alcohol (2) or tetrahydrofuran to provide compounds of formula (I).

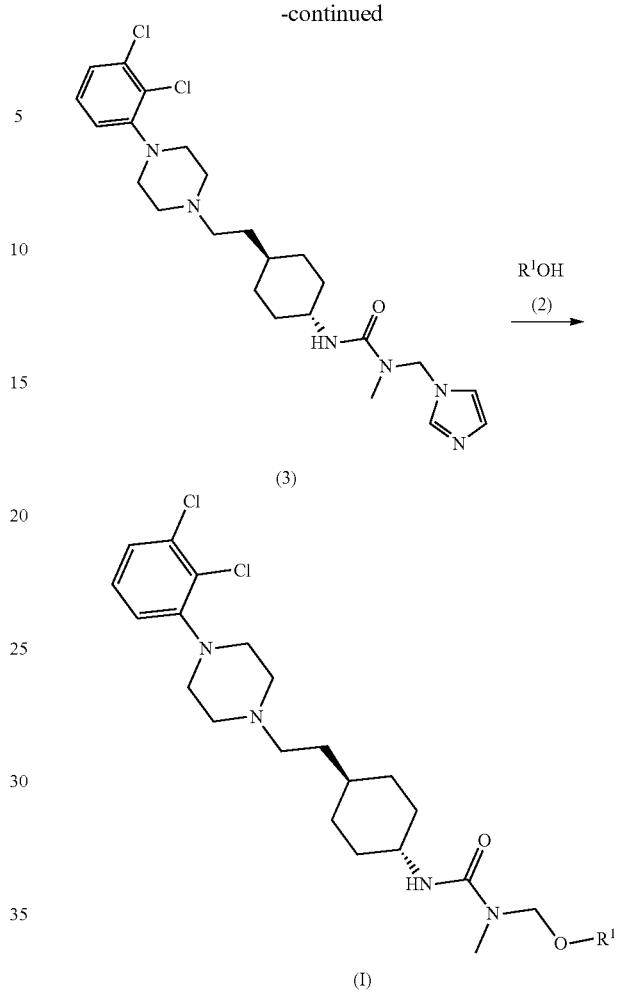

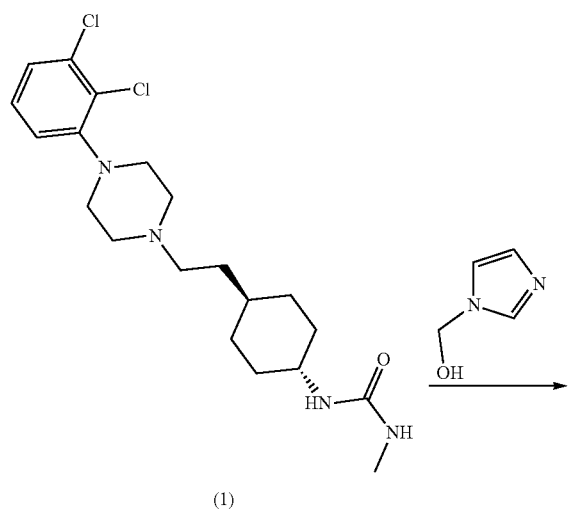

Scheme 2

(1)

As shown in Scheme 2, compounds of formula (I) can be prepared from the compound of formula (1). Accordingly, the compound of formula (1) can be treated with commercially available 1-hydroxymethyl imidazole at ambient temperature to reflux for 1 to 24 hours in a suitable solvent, such as a mixture of acetic acid and tetrahydrofuran to provide the compound of formula (3). The compound of formula (3) can be treated with the appropriate alcohol of formula (2), wherein R¹ is as described herein, in the presence of a suitable base such as potassium hydroxide or a suitable acid such as sulfuric acid or methanesulfonic acid to provide compounds of formula (I). The reaction is typically performed at ambient temperature to reflux for 1 to 24 hours in a suitable solvent such as tetrahydrofuran or toluene.

Specific procedures are provided in the Synthetic Examples section. Unless otherwise described, the starting materials and reagents are either commercially available or may be prepared by one skilled in the art from commercially available materials using methods described in the chemical literature.

Pharmaceutical Compositions

When employed as a pharmaceutical, a compound of the present disclosure may be administered in the form of a pharmaceutical composition. Such composition may comprise a therapeutically effective amount of a compound of Formula (I), or a pharmaceutically acceptable salt thereof, together with a pharmaceutically acceptable carrier.

9

In some embodiments, a pharmaceutical composition is provided comprising a therapeutically effective amount of a compound of Formula (I), or a pharmaceutically acceptable salt thereof, in combination with a pharmaceutically acceptable carrier.

Method of Use

The compounds of Formula (I), or pharmaceutically acceptable salts thereof, and pharmaceutical compositions comprising a compound of Formula (I), or a pharmaceutically acceptable salt thereof, may be administered to a subject suffering from schizophrenia. The term "administering" refers to the method of contacting a subject with a compound.

In some embodiments, the present disclosure provides for the compounds of Formula (I), or pharmaceutically acceptable salts thereof, and pharmaceutical compositions comprising a compound of Formula (I), or a pharmaceutically acceptable salt thereof, for use as a medicament.

In some embodiments, the present disclosure provides for the compounds of Formula (I), or pharmaceutically acceptable salts thereof, and pharmaceutical compositions comprising a compound of Formula (I), or a pharmaceutically acceptable salt thereof, for use in the treatment of schizophrenia.

In some embodiments, the present disclosure provides for the use of the compounds of Formula (I), or pharmaceutically acceptable salts thereof, and pharmaceutical compositions comprising a compound of Formula (I), or a pharmaceutically acceptable salt thereof, for the manufacture of a medicament for the treatment of schizophrenia.

EXAMPLES

The following Examples may be used for illustrative purposes and should not be deemed to narrow the scope of the invention.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference.

The following abbreviations have the indicated meaning unless otherwise specified:

| | |
|---|---|
| NMR | Nuclear Magnetic Resonance |
| s | Singlet |
| br s | Broad singlet |
| d | Duplet or Doublet |
| m | Multiplet |
| t | Triplet |
| q | Quartet |
| sxt | Sextet |
| LC/MS or LCMS | Liquid Chromatography-Mass Spectrometry |
| min | Minute |
| mL | Milliliter |
| μL | Microliter |
| L | Liter |
| g | Gram |
| mg | Milligram |
| mmol | Millimoles |
| HPLC | High Pressure Liquid Chromatography |
| ppm | Parts per million |
| ESI | Electrospray Ionization |
| M | Molarity (moles/liter) |

Synthetic Examples

Example 1

N'-[(1r,4r)-4-{2-[4-(2,3-dichlorophenyl)piperazin-1-yl]ethyl}cyclohexyl]-N-(ethoxymethyl)-N-methylurea A mixture of 5.0 g (12.5 mmol) of N-[(1r,4r)-4-{2-[4-(2,3-dichlorophenyl)piperazin-1-yl]ethyl}cyclohexyl]-N-methylurea, 250 mL of ethanol, 2.5 mL of acetic acid and 3.75 g (125 mmol) of paraformaldehyde was stirred for 40 hours at 70° C. The reaction mixture was concentrated in vacuo. The residue was chromatographed on silica gel eluting with acetone. The crude material was mixed with diethyl ether and filtered to provide the title compound. $^1$H NMR (400 MHz, DMSO-d$_6$) δ ppm 0.88-1.02 (m, 2H), 1.08 (t, J=7.0 Hz, 3H), 1.14-1.28 (m, 3H), 1.31-1.40 (m, 2H), 1.69-1.81 (m, 4H), 2.31-2.39 (m, 2H), 2.42-2.61 (br m, 4H), 2.79 (s, 3H), 2.90-3.04 (br m, 4H), 3.35 (q, J=7.0 Hz, 2H), 3.31-3.44 (m, 1H), 4.63 (s, 2H), 6.03 (d, J=7.8 Hz, 1H), 7.10-7.18 (m, 1H), 7.25-7.34 (m, 2H); LC-MS (ESI) m/z 471.3 (M+H)$^+$.

Example 2

N'-[(1r,4r)-4-{2-[4-(2,3-dichlorophenyl)piperazin-1-yl]ethyl}cyclohexyl]-N-(methoxymethyl)-N-methylurea A mixture of 1 g (2.4 mmol) of N-[(1r,4r)-4-{2-[4-(2,3-dichlorophenyl)piperazin-1-yl]ethyl}cyclohexyl]-N-methylurea, 20 mL of methanol, 0.5 mL of acetic acid and 2 mL (26.8 mmol) of 37% formaldehyde solution (aqueous with ~10% methanol) was stirred for 20 hours at 85° C. The reaction mixture was concentrated in vacuo. The residue was purified by preparative HPLC on Phenomenex Kinetex® 5 μm C18 100 Å AXIA Packed LC Column (150 mm×21.2 mm); isocratic of 20 mmol/L NH$_4$HCO$_3$ in water+0.1% diethylamine (A) over 3 minutes; 40-50% gradient of 20 mmol/L NH$_4$HCO$_3$ in water+0.1% diethylamine (A) and methanol (B) over 16 minutes, at a flow rate 21.2 mL/minute, at 40° C. to provide the title compound. $^1$H NMR (400 MHz, dimethyl sulfoxide-d$_6$) δ ppm 0.88-1.06 (m, 2H), 1.15-1.28 (m, 3H), 1.31-1.40 (m, 2H), 1.68-1.82 (m, 4H), 2.31-2.39 (m, 2H), 2.46-2.59 (br m, 4H), 2.79 (s, 3H), 2.90-3.05 (br m, 4H), 3.12 (s, 3H), 3.25-3.45 (m, 1H), 4.59 (s, 2H), 6.05 (d, J=7.9 Hz, 1H), 7.11-7.17 (m, 1H), 7.27-7.34 (m, 2H); LC-MS (ESI) m/z 457.3 (M+H)$^+$.

Example 3

N'-[(1r,4r)-4-{2-[4-(2,3-dichlorophenyl)piperazin-1-yl]ethyl}cyclohexyl]-N-methyl-N-(propoxymethyl)urea Example 3A N'-[(1r,4r)-4-{2-[4-(2,3-dichlorophenyl)piperazin-1-yl]ethyl}cyclohexyl]-N-[(1H-imidazol-1-yl)methyl]-N-methylurea A mixture of 3.0 g (7.25 mmol) of N-[(1r,4r)-4-{2-[4-(2,3-dichlorophenyl)piperazin-1-yl]ethyl}cyclohexyl]-N-methylurea, 1.070 g (10.9 mmol) of (1H-imidazol-1-yl)methanol, 9 mL (200 mmol) of acetic acid and 70 mL of tetrahydrofuran was stirred at 80° C. for 18 hours. Dichloromethane (100 mL) and 50 mL of saturated aqueous NaHCO₃ solution were added to the mixture. The organic layer was separated, dried over sodium sulfate, and filtered. The filtrate was concentrated in vacuo. The residue was mixed with mixture of diethyl ether (200 mL) and methanol (5 mL) and filtered to provide the title compound. LC-MS (ESI) m/z 493.3 (M+H)⁺.

Example 3B

N-'[(1r,4r)-4-{2-[4-(2,3-dichlorophenyl)piperazin-1-yl]ethyl}cyclohexyl]-N-methyl-N-(propoxymethyl) urea To a solution of 87 mg of methanesulfonic acid (0.9 mmol) in 273 mg of 1-propanol (4.55 mmol), 20 mL of toluene and 443 mg (1 mmol) of N-[(1r,4r)-4-{2-[4-(2,3-dichlorophenyl)piperazin-1-yl]ethyl}cyclohexyl]-N-[(1H-imidazol-1-yl)methyl]-N-methylurea were added at room temperature and the reaction mixture was stirred at 90° C. for 2 hours. Ethyl acetate (30 mL) and 30 mL of saturated aqueous NaHCO₃ solution were added to the mixture. The organic layer was separated, dried over sodium sulfate, and filtered. The filtrate was concentrated in vacuo. The residue was chromatographed on silica gel, eluting with dichloromethane/methanol (97:3). The crude material was mixed with n-pentane and filtered to provide the title compound. ¹H NMR (400 MHz, DMSO-d₆) δ ppm 0.84 (t, J=7.2 Hz, 3H), 0.88-1.03 (m, 2H), 1.13-1.29 (m, 3H), 1.30-1.40 (m, 2H), 1.48 (sxt, J=7.0 Hz, 2H), 1.69-1.81 (br m, 4H), 2.31-2.40 (m, 2H), 2.43-2.60 (br m, 4H), 2.79 (s, 3H), 2.90-3.05 (br m, 4H), 3.26 (t, J=6.5 Hz, 2H), 3.31-3.46 (m, 1H), 4.64 (s, 2H), 6.02 (d, J=7.8 Hz, 1H), 7.11-7.17 (m, 1H), 7.27-7.33 (m, 2H); LC-MS (ESI) m/z 485.3 (M+H)⁺.

Reference Example 1

N'-[(1r,4r)-4-{2-[4-(2,3-dichlorophenyl)piperazin-1-yl]ethyl}cyclohexyl]-N-methyl-N-propylurea The title compound was prepared as described in WO2005012266

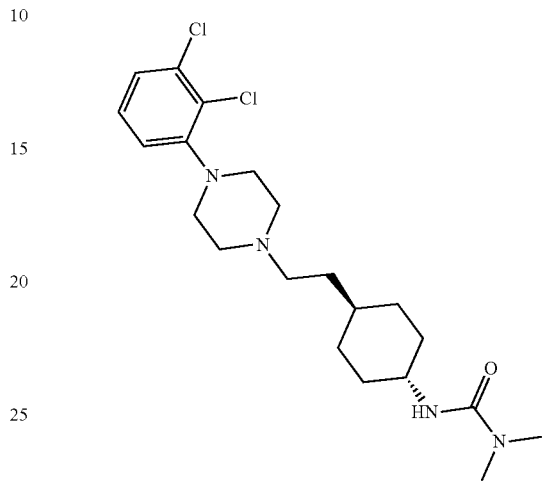

Reference Example 2

N'-[(1r,4r)-4-{2-[4-(2,3-dichlorophenyl)piperazin-1-yl]ethyl}cyclohexyl]-N,N-dimethylurea (CAR)

The title compound was prepared as described in WO2005012266.

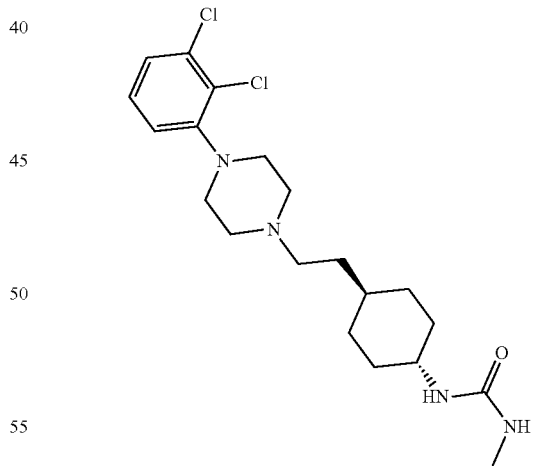

Reference Example 3

N'-[(1r,4r)-4-{2-[4-(2,3-dichlorophenyl)piperazin-1-yl]ethyl}cyclohexyl]-N-methylurea (DCAR)

The title compound was prepared as described in WO2005012266.

Kinetic Solubility Study

| DMSO solubility class | Maximal concentration in kinetic solubility study (µM)* |
|---|---|
| Soluble ≥ 10 mM | 100 |
| Moderate ≥ 5 mM | 50 |
| Low ≥ 1 mM | 10 |
| Insoluble < 1 mM | not measured |

*In the presence of 1% DMSO co-solvent, RT, 2 hours

For determination of kinetic solubility, 3 mL of a 10 mM (5 mM, 1 mM) DMSO stock solution of each compound was pipetted into a well of a 96 well plate (Millipore Multiscreen®$_{HTS}$-PCF Filter Plate, MilliporeSigma, St. Louis, MO, USA) which contained 295 mL of PBS pH 7.4. Following shaking of the suspension on an orbital shaker at 300 rpm for 2 hours, the suspension was clarified by vacuum filtration (Multiscreen® Vacuum Manifold; MilliporeSigma). Immediately following the filtration step, 160 mL of the filtrate was transferred into 40 mL of acetonitrile to avoid compound precipitation from the saturated solution. The concentration of the research compound was determined by HPLC-UV-(MS) detection, by using an external standard made from the same batch of research compound. Results are shown in Table 2.

Thermodynamic Solubility Study (37° C., 4 Hours)

For measuring thermodynamic solubility: typically, 200-400 µL of the solution were added to 1-2 mg of the solid test materials (n=5). The resulted mixtures/oversaturated solutions are shaken at 37° C. for 4 hrs (to the solution equilibrium) and are filtrated on a Millipore MultiSreen Filter Plate (0.45 µm). Concentrations of the filtrates are determined by LC/UV/MS based on a 5-point calibration. (When the solid material dissolved totally in the aqueous test medium the result should be considered as a minimal value.) Results are shown in Table 2.

Thermodynamic Solubility Study (RT, 24 Hours)

For measuring thermodynamic solubility: typically, 200-400 µL of the solution were added to 1-2 mg of the solid test materials (n=5). The resulted mixtures were shaken at room temperature (RT) for 24 hrs (to the solution equilibrium) and were filtrated on a Millipore MultiScreen Filter Plate (0.45 µm). Concentrations of the filtrates were determined by LC/UV/MS based on a 5-point calibration. (When the solid material dissolved totally in the aqueous test medium the result should be considered as a minimal value.) Results are shown in Table 2.

TABLE 2

| | Kinetic sol. [µM] PBS pH = 7.4 2 hours, RT | Thermo-dynamic sol. [µM] SIF pH = 6.8 4 hours, 37° C. | Thermo-dynamic sol. [µM] PBS pH = 7.4 4 hours, 37° C. | Thermo-dynamic sol. [µM] PBS pH = 7.4 24 hours, RT |
|---|---|---|---|---|
| Example 1 | 72.7 ± 3.4 | 53.5 ± 0.9 | 10.9 ± 0.3 | 45.3 ± 0.6 |
| Example 2 | 47.7 ± 4.5 | 147.04 ± 8.72 | 58.93 ± 5.32 | 50.93 ± 2.3 |
| Example 3 | 32.4 ± 3.2 | 32.68 ± 1.65 | 30.50 ± 3.06 | 39.68 ± 2.15 |
| Ref. Ex. 1 | 10.9 ± 1.7 | 27.7 ± 1.1 | 4.9 ± 0.3 | 6.2 ± 0.3 |
| Ref. Ex. 2 | 7.8 ± 0.1 | 13.3 ± 1.5 ** | 3.2 ± 0.3 ** | 3.8 ± 0.3 |
| Ref. Ex. 3 | 0.9 ± 0.1 | 1.9 ± 0.2 ** | 0.3 ± 0.1 ** | 0.6 ± 0.1 |

SIF: pH 6.8 Simulated Intestinal Fluid without pancreatin (0.68% (w/v) KH$_2$PO$_4$, 0.09% (w/v) NaOH)
PBS: pH 7.4 (0.01M phosphate buffered saline, 0.138M NaCl, 0.0027M KCl, without Ca$^{2+}$, Mg$^{2+}$)
** 24 hours
RT = room temperature The kinetic and thermodynamic solubility data of the Examples of the present disclosure indicate that their solubility compared to that of the reference compounds is unexpectedly improved.

Biological Assays

In the in vitro biology studies, the following abbreviations were commonly used: BSA for bovine serum albumin, cAMP for cyclic adenosine monophosphate, DMEM for Dulbecco's modified Eagle's medium, DMSO for dimethyl sulfoxide, EDTA for Ethylenediaminetetraacetic acid tetra-sodium salt, EGTA for Ethylene glycol-bis(2-aminoethylether)-N,N,N',N'-tetraacetic acid, FBS for fetal bovine serum, G418 for geneticin, IBMX for 3-isobutyl-1-methylxanthine, and Tris for tris(hydroxymethyl)aminomethane.

Studies with Human $D_{2L}$ Receptors

Determination of Affinity of Human $D_{2L}$ Receptors in Competitive Binding Assay using [$^3$H]raclopride Cultured CHO-K1 cells expressing recombinant human $D_{2L}$ receptors (DRD2L cAMP Hunter™, $G_i$ cell line, Eurofins DiscoverX, Fremont, CA, USA) were homogenized in 4× (v/v) buffer solution (50 mM Tris, 5 mM MgCl$_2$, 1 mM EGTA, pH 7.4 at 25° C.) with a Dounce tissue grinder and centrifuged at 40,000×g at 4° C. for 10 minutes. The supernatant was removed, and the pellet was resuspended in 4× buffer (v/v) and centrifuged. The resulting pellet was resuspended in the above buffer solution at a volume of 12.5 mL/g original weight. The membrane preparation was then aliquoted and stored at −70° C.

Test compounds were diluted serially in DMSO and subsequently diluted to 5% DMSO (v/w) in binding buffer (50 mM Tris, 5 mM MgCl$_2$, 5 mM KCl, 1 mM CaCl$_2$), 120 mM NaCl, 1 mM EDTA). A 5× concentrated compound in binding buffer (50 µL) was transferred into 96 well deep-well plates (BRAND, Wertheim, Germany). Aliquoted membrane preparations were thawed and washed once in binding buffer. In the same buffer, 10 µg protein/well was incubated with 2 nM [$^3$H]raclopride (PerkinElmer, Waltham, MA, USA) in the presence or absence of test compound (to determine the binding inhibition of the test compound or the total binding, respectively) for 120 minutes at 25° C. in a volume of 250 µL. Non-specific binding (NSB) was determined in the presence of 10 µM haloperidol, an antagonist of the D$_2$ receptor. After incubation, samples were filtered over UniFilter® GF/B plates (PerkinElmer) using a Filtermate™ harvester (PerkinElmer) and washed four times with 1 mL ice-cold binding buffer. The plates were dried at 40° C. for an hour and 40 µL Microscint™-20 scintillation cocktail (PerkinElmer) was added to each well. The radioactivity was determined using a MicroBeta$^2$® microplate counter (PerkinElmer).

Non-specific binding was subtracted to yield specific binding which was normalized to vehicle-treated samples and converted to displacement % values. GraFit 6.0 (Erithracus Software, Horley, UK) was used for determination of $IC_{50}$ values and curve fittings. $IC_{50}$ values (i.e., concentration of compound giving 50% inhibition of specific binding) were determined from concentration-displacement curves by sigmoidal fitting. The inhibition constants ($K_i$) were calculated using the Cheng-Prusoff equation: $K_i=IC_{50}/[1+([L]/K_D)]$, where [L] is the radioligand concentration and $K_D$ the affinity of the labeled ligand for receptor. $K_D$ was determined from a separate saturation experiment. The $pK_i$ value was derived by calculating the negative logarithm of the $K_i$ value expressed in mol/liter. Experiments were performed in triplicates, and results are shown in Table 3. The results indicate that the examples of the present disclosure are high affinity ligands of human recombinant $D_{2L}$ receptors.

TABLE 3

| Example | $D_{2L}$ $pK_i$ [$^3$H]raclopride |
|---|---|
| 1 | 8.71 |
| 2 | 8.90 |
| 3 | 8.94 |
| Ref. Ex. 2 | 8.71 |

Determination of Affinity of Human $D_{2L}$ Receptors in Competitive Binding Assay Using [3H]Spiperone CHO-K1 cells expressing human recombinant $D_{2L}$ receptors were washed with phosphate-buffered saline (PBS). Cells were scraped from the plates and centrifuged at 1000×g. Cells were disrupted using a Teflon® pestle homogenizer in buffer containing 25 mM Tris-HCl, pH=7.4, 6 mM $MgCl_2$, 1 mM EDTA, 10 mM phenylmethylsulfonyl fluoride (PMSF). The resulting suspension was centrifuged at 1000×g. The supernatant was collected and centrifuged at 41,000×g. The supernatant was discarded, and the pellet was resuspended in above buffer. The membrane preparation was then aliquoted and stored at −70° C.

Aliquoted membrane preparations were incubated with 0.16 nM [$^3$H]spiperone (PerkinElmer) in the presence or absence of test compound in 96-well plates for 120 minutes at 25° C. in an incubation buffer containing 50 mM Tris-HCl, 1.4 mM ascorbic acid, 0.001% BSA, 150 mM NaCl, pH 7.4, with 1% DMSO in a final reaction volume of 222 µL. Non-specific binding (NSB) was determined in the presence of 10 µM haloperidol (Sigma-Aldrich). After incubation, samples were filtered over UniFilter® GF/C plates (PerkinElmer), washed and Microscint™-20 scintillation cocktail was added. Radioactivity was determined with a MicroBeta$^2$® microplate counter (PerkinElmer).

From scintillation counts, NSB was subtracted to yield specific binding which was normalized to vehicle-treated samples and converted to displacement % values. $IC_{50}$ values were determined by a non-linear, least squares regression analysis using MathIQ™ (ID Business Solutions Ltd., Surrey, UK). $K_i$ values were calculated using the Cheng-Prusoff equation using the observed $IC_{50}$ of the tested compound, the concentration of radioligand employed in the assay, and the historical values for the $K_D$ of the ligand. The $pK_i$ value was derived by calculating the negative logarithm of the $K_i$ value expressed in mol/liter and is shown in Table 4. The results indicate that the examples of the present disclosure are high affinity ligands of human recombinant $D_{2L}$ receptors when using [$^3$H]spiperone as a radioligand.

TABLE 4

| Example | $D_{2L}$ $pK_i$ [$^3$H]spiperone |
|---|---|
| 1 | 9.06 |
| 2 | 8.93 |
| 3 | 8.93 |
| Ref. Ex. 2 | 9.20 |

Characterization of Agonism of Human $D_{2L}$ Receptors Using Cyclic Adenosine Monophosphate Detection Agonist activity at human $D_{2L}$ receptors was assayed by measuring cAMP levels in CHO-K1 cells expressing human $D_{2L}$ receptors (Eurofins DiscoverX, Fremont, CA, USA) by homogenous time-resolved fluorescence (HTRF®) using the cAMP $G_i$ kit (Cisbio/PerkinElmer). CHO-K1 cells expressing human $D_{2L}$ receptors were cultured in Ham's F12 medium supplemented with 10% FBS, 1% penicillin-streptomycin antimycotic solution, and 800 µg/mL G418 (Thermo Fisher Scientific, Waltham, MA, USA) and maintained at 37° C. in a humidified atmosphere containing 5.0% $CO_2$. For the cAMP measurements, cryopreserved cells were thawed, and seeded in white-walled, half area 96-well plates at 10,000 cells/well in PathHunter® AssayComplete™ Cell Plating 2 (CP2) reagent (Eurofins DiscoverX) and incubated overnight at 37° C. in a humidified atmosphere with 5.0% $CO_2$. Prior to the cAMP measurement, the CP2 reagent was removed from the cells and replaced with 20 µL compound or vehicle containing assay buffer (140 mM NaCl, 5 mM KCl, 2 mM $MgCl_2$, 2 mM $CaCl_2$), 10 mM 2-[4-(2-hydroxyethyl)piperazin-1-yl]ethane-1-sulfonic acid (HEPES), 10 mM glucose, pH 7.4) supplemented with 100 µM IBMX and incubated at ambient temperature for 20 minutes. After an additional 30-minute incubation step at ambient temperature with 0.5 µM forskolin (Eurofins DiscoverX), cell stimulation was stopped by adding the detection reagents (20 µL cAMP-d2 and 20 µL anti-cAMP cryptate, Cisbio/PerkinElmer) diluted in lysis buffer. The time-resolved fluorescence signal was quantified with a PHERAstar FS multimode reader (BMG Labtech, Ortenberg, Germany) using standard HTRF® settings with laser excitation at 337 nm after 60 minutes of incubation at ambient temperature. Results were calculated from the ratio of acceptor fluorescence signal (A665 nm) and donor fluorescence signal (A620 nm)×$10^4$ and expressed as ΔF % values using the following formula: 100×(Ratio Sample-Ratio Negative Control)/Ratio Negative Control. In experiments, all treatments were measured in multiple wells in parallel, and the mean ΔF % values were used for further analysis. Agonist activity values were calculated as percentage of inhibition of forskolin-stimulated cAMP accumulation normalized to the response evoked by a maximally effective concentration of dopamine tested in the same experiment. All calculations were done using Microsoft Excel® (Microsoft, Redmond, WA, USA). The $pEC_{50}$ values shown in Table 5 (the negative logarithm of the concentration, expressed in mol/liter, of the agonist that produces 50% inhibition of forskolin-stimulated cAMP accumulation) were obtained by fitting 4-parameter sigmoidal curves to the concentration-effect data with the lower asymptote constrained to zero using GraphPad Prism (GraphPad, San Diego, CA, USA). The results indicate that the examples of the present disclosure are potent agonists of the G-protein-coupled signaling pathway of human recombinant $D_{2L}$ receptors.

TABLE 5

| Example | $D_{2L}$ cAMP $pEC_{50}$ |
|---|---|
| 1 | 8.43 |
| 2 | 8.88 |
| Ref. Ex. 2 | 8.43 |

Measurement of β-Arrestin Recruitment to Human Dopamine $D_{2L}$ Receptors

PathHunter® CHO-K1 cells expressing tagged human $D_{2L}$ receptors and tagged β-arrestin-2 (Eurofins DiscoverX, Fremont, CA, USA) were seeded into 96-well white-walled clear bottom tissue culture plates in 90 μL/cell AssayComplete™ Cell Plating 2 (CP2) reagent (Eurofins DiscoverX) at a density of 20,000 cells/well. The plates were incubated overnight in a humidified atmosphere with 5% $CO_2$ at 37° C. Twenty to twenty-four hours later, 20 μL of test compound or vehicle in CP2 reagent and containing 2.2% DMSO was added to the cells, and they were incubated for 90 minutes at 37° C. Then, 55 μL PathHunter® Detection Reagent (Eurofins DiscoverX) was added per well and plates were incubated for 60 minutes at 25° C., followed by luminescence detection using a PHERAstar® FS multimode plate reader (BMG Labtech, Ortenberg, Germany). Raw data were converted to percent stimulation above basal values. Values were further converted to percent of maximal stimulation of β-arrestin recruitment by 30 μM dopamine. $EC_{50}$ values were calculated from concentration-response curves of at least six concentrations run in duplicates by sigmoidal fitting using Origin® 7.5 software (OriginLab Corporation, Northampton, MA, USA) and were defined as the concentration of the agonist with half-maximal stimulation. The $pEC_{50}$ values were calculated as the negative logarithm of the $EC_{50}$ value expressed in mol/liter and is shown in Table 6. The results indicate that the examples of the present disclosure are potent agonists of the G-protein-independent signaling pathway of human recombinant $D_{2L}$ receptors.

TABLE 6

| Example | $D_{2L}$ arrestin $pEC_{50}$ |
|---|---|
| 1 | 8.96 |
| 2 | 9.14 |
| Ref. Ex. 2 | 8.71 |

Studies with Human $D_3$ Receptors
Determination of Affinity at Human $D_3$ Receptors in Competitive Binding Assay Using [$^3$H]raclopride Cell cultures (CHO-K1) expressing recombinant human $D_3$ receptors (DRD3, GenBank ID U32499, purchased from Euroscreen Fast, Brussels, BE) were homogenized in 4× buffer (v/v) solution (15 mM Tris, 2 mM $MgCl_2$, 0.3 mM EDTA, 1 mM EGTA, pH 7.4 at 25° C.) with a Dounce tissue grinder and centrifuged at 40,000×g at 4° C. for 25 minutes. The supernatant was removed, and the pellet was resuspended in 4× (v/v) buffer and centrifuged. The process was repeated twice, and the pellet was resuspended in storage buffer (75 mM Tris, 12.5 mM $MgCl_2$, 0.3 mM EDTA, 1 mM EGTA, 250 mM sucrose, pH 7.4 at 25° C.) at a volume of 12.5 mL/g original cell weight. The membrane preparation was then aliquoted and stored at −70° C.

Compounds were diluted in DMSO and binding buffer (containing 50 mM Tris, 5 mM $MgCl_2$, 5 mM KCl, 1 mM $CaCl_2$), 120 mM NaCl, 1 mM EDTA) and 50 μL of each solution was transferred into a deep-well plate (BRAND) in 5-fold final concentration in 5% DMSO-buffer solution. The aliquoted membrane preparation was thawed and washed once in binding buffer. In the same buffer, 3.3 μg protein/assay was incubated with ca. 2.7 nM [$^3$H]raclopride (PerkinElmer) in the presence or absence of test compound for 120 minutes at 25° C. in a volume of 250 μL in a 96-well deep well plate (BRAND). Non-specific binding (NSB) was determined in the presence of 10 μM haloperidol. DMSO final concentration was 1% (v/v) in all reactions. After incubation, samples were filtered over UniFilter® GF/B plates (PerkinElmer) using a Filtermate™ harvester (PerkinElmer) and washed with 4×1 mL ice-cold binding buffer. The plate was dried at 40° C. for an hour and 40 μL Microscint™-20 scintillation cocktail (PerkinElmer) was added to each well. Radioactivity was determined with a Microbeta$^2$® microplate counter (PerkinElmer).

Using raw scintillation counts, NSB was subtracted to yield specific binding which was normalized to vehicle-treated samples and converted to displacement percent values. GraFit 6.0 (Erithracus Software, Horley, UK) was used for curve fittings and calculations. $IC_{50}$ values (i.e., concentration of compound giving 50% inhibition of specific binding) were determined from concentration-displacement curves by sigmoidal fitting. The inhibition constants ($K_i$) were calculated using the Cheng-Prusoff equation: $K_i=IC_{50}/[1+([L]/K_D)]$, where [L] is the radioligand concentration and $K_D$ the affinity of the labeled ligand for receptor. $K_D$ was determined from a separate saturation experiment. The $pK_i$ value shown in Table 7 was derived by calculating the negative logarithm of the $K_i$ value expressed in mol/liter. In all experiments, samples were run in triplicate. The results indicate that the examples of the present disclosure are high affinity ligands of human recombinant $D_3$ receptors.

TABLE 7

| Example | $D_3$ $pK_i$ [$^3$H]raclopride |
|---|---|
| 1 | 8.99 |
| 2 | 9.15 |
| Ref. Ex. 2 | 9.51 |

Determination of Affinity at Human $D_3$ Receptors in Competitive Binding Assay Using [$^3$H]spiperone CHO-K1 cells expressing human recombinant $D_3$ receptors were washed with PBS. Cells were scraped from the plates and centrifuged at 1000×g. Cells were disrupted using a Teflon® pestle homogenizer in buffer containing 25 mM Tris-HCl, pH=7.4, 6 mM $MgCl_2$, 1 mM EDTA, 10 mM PMSF. The suspension was centrifuged at 1000×g. The supernatant was collected and centrifuged at 41,000×g. The supernatant was discarded, and the pellet was resuspended in above buffer. The membrane preparation was aliquoted and stored at −70° C.

Aliquoted membrane preparations were incubated with 0.7 nM [$^3$H]spiperone (PerkinElmer) in the presence or absence of test compound in 96-well plates for 120 minutes at 37° C. in an incubation buffer containing 50 mM Tris-HCl, 1.4 mM ascorbic acid, 0.001% bovine serum albumin, and 150 mM NaCl, at pH 7.4, with 1% DMSO in a final reaction volume of 222 L. Non-specific binding (NSB) was determined in the presence of 25 μM (S)-(−)-sulpiride (Sigma Aldrich). After incubation, samples were filtered on GF/C filter plates (PerkinElmer), washed, and Microscint™-20 scintillation cocktail was added. Radioactivity was determined in a MicroBeta$^2$® microplate counter (PerkinElmer).

From raw scintillation counts, NSB was subtracted to yield specific binding which was normalized to vehicle-treated samples and converted to displacement % values. $IC_{50}$ values were determined by a non-linear, least squares regression analysis using MathIQ™ (ID Business Solutions Ltd., Surrey, UK). $K_i$ values were calculated using the Cheng-Prusoff equation using the observed $IC_{50}$ of the tested compound, the concentration of radioligand employed in the assay, and the historical values for the $K_D$ of the ligand. The $pK_i$ value shown in Table 8 was derived by calculating the negative logarithm of the $K_i$ value expressed in mol/liter. The results indicate that the examples of the present disclosure are high affinity ligands of human recombinant $D_3$ receptors when using [$^3$H]spiperone as a radioligand.

TABLE 8

| Example | $D_3$ $pK_i$ [$^3$H] spiperone |
|---|---|
| 1 | 10.00 |
| 2 | 9.77 |
| 3 | 9.74 |
| Ref. Ex. 2 | 9.80 |

Characterization of Agonism at Human $D_3$ Receptors Using Cyclic Adenosine Monophosphate Detection Agonist activity at human $D_3$ receptors was assayed by cAMP levels in HEK293 cells expressing recombinant human $D_3$ receptors (BioXtal, Saint-Félix, France) stably co-expressing adenylyl cyclase V (ACV) (cell line developed by Gedeon Richter) by homogenous time-resolved fluorescence (HTRF) using the cAMP $G_i$ kit (Cisbio/PerkinElmer). HEK293 cells expressing recombinant human $D_3$ receptors and ACV were cultured in DMEM supplemented with 10% FBS, 1% penicillin-streptomycin antimycotic solution, 1% pyruvate, 100 µg/mL G418 (Thermo Fisher Scientific) and 60 µg/mL hygromycin B and maintained at 37° C. in a humidified atmosphere containing 5% $CO_2$. Prior to measuring cAMP, cells were detached with Versene (Thermo-Fisher Scientific) and resuspended in assay buffer (140 mM NaCl, 5 mM KCl, 2 mM $MgCl_2$, 2 mM $CaCl_2$), 10 mM 2-[4-(2-hydroxyethyl)piperazin-1-yl]ethane-1-sulfonic acid (HEPES), 10 mM glucose, pH 7.4) in white-walled, half area 96-well microplates at a density of 15,000 cells/well and 20 µL volume. The assay buffer was supplemented with 100 µM IBMX (Sigma Aldrich, St Louis, MO, USA). After adding the test compounds (4× concentrated) or vehicle (DMSO) at 10 µL/well, cells were incubated with assay buffer or various concentrations of the test compounds for 20 minutes. After an additional 30 minutes incubation at ambient temperature with 1.5 µM forskolin (DMSO final concentration was 0.3%) cell stimulation was stopped by adding detection reagents (20 µL cAMP-d2 and 20 µL anti-cAMP cryptate) diluted in lysis buffer (PerkinElmer). The time-resolved fluorescence (TRF) signal was quantified with a PHERAstar FS multimode reader (BMG Labtech, Ortenberg, Germany) using standard HTRF settings with laser excitation at 337 nm after 60 minutes of incubation at ambient temperature.

Results were calculated from the ratio of acceptor fluorescence signal (A665 nm) and donor fluorescence signal (A620 nm)×$10^4$ and expressed as ΔF % values using the following formula: 100× (ratio sample-ratio negative control)/ratio negative control. In all experiments multiple wells were measured in parallel, and the mean ΔF % values were used for further analysis. Agonist activity values were calculated as percentage of inhibition of forskolin-stimulated cAMP accumulation normalized to the response evoked by a maximally effective concentration of dopamine tested in the same experiment. All calculations were done using Excel (Microsoft, Redmond, WA, USA). The $pEC_{50}$ values (the negative logarithm of the concentration, expressed in mol/liter, of the agonist that produces 50% inhibition of forskolin-stimulated cAMP accumulation) were obtained by fitting 4-parameter sigmoidal curves to the concentration-effect data with the lower asymptote constrained to zero using GraphPad Prism (GraphPad Software, San Diego, CA, USA) and are shown in Table 9. The results indicate that the examples of the present disclosure are highly potent agonists of the G-protein-dependent signaling pathway of human recombinant $D_3$ receptors.

TABLE 9

| Example | $D_3$ cAMP $pEC_{50}$ |
|---|---|
| 1 | 8.45 |
| 2 | 8.71 |
| Ref. Ex. 2 | 8.71 |

Measurement of β-Arrestin Recruitment to Human Dopamine $D_3$ Receptors

PathHunter® CHO-K1 cells expressing tagged human $D_3$ receptors and tagged β-arrestin-2 (Eurofins DiscoverX, Fremont, CA, USA) were seeded into 96-well white-walled clear bottom tissue culture plates in 90 µL AssayComplete™ Cell Plating 2 (CP2) reagent (Eurofins DiscoverX) at a density of 25,000 cells/well and incubated overnight in humidified atmosphere with 5% $CO_2$ at 37° C. Twenty to twenty-four hours later, 20 µL of test compounds or vehicle in CP2 reagent containing 2.2% DMSO was added to the cells and the cells were incubated for 90 minutes at 37° C. Following incubation, 55 µL PathHunter® Detection Reagent (Eurofins DiscoverX) was added per well and the plates were incubated for 60 minutes at 25° C. followed by luminescence detection using a PHERAstar® FS multimode plate reader (BMG Labtech, Ortenberg, Germany).

Raw data were first converted to stimulation % above basal values. The stimulation % above basal values were further converted to % of maximal stimulation of β-arrestin recruitment by 1 µM dopamine. $EC_{50}$ values were calculated from concentration-response curves of at least six concentrations in duplicates by sigmoidal fitting using Origin® 7.5 software (OriginLab© Corporation, Northampton, MA, USA) and were defined as the concentration of the agonist with half-maximal stimulation. The $pEC_{50}$ values shown in Table 10 were calculated as the negative logarithm of the $EC_{50}$ value expressed in mol/liter. The results indicate that the examples of the present disclosure are highly potent agonists of the G-protein-independent signaling pathway of human recombinant $D_3$ receptors.

TABLE 10

| Example | $D_3$ arrestin $EC_{50}$ |
|---|---|
| 1 | 8.51 |
| 2 | 8.41 |
| Ref. Ex. 2 | 8.55 |

5-$HT2_A$ Receptor Assays
Determination of Affinity for Human 5-$HT_{2A}$ Receptors in Competitive Binding Assay Receptor membranes were prepared from the CHO-K1 recombinant AequoScreen® cell line stably expressing the human 5-$HT_{2A}$ receptor (PerkinElmer, Waltham, MA, USA). Cells were suspended in 4× volume in buffer A (15 mM Tris-HCl, pH 7.5, 2 mM $MgCl_2$, 0.3 mM EDTA, 1 mM EGTA) (1 g cell-4 mL buffer) and homogenized in a Dounce homogenizer. The crude membrane fraction was collected following two consecutive centrifugation steps at 40,000×g for 25 minutes separated by a washing step in buffer A. The final pellet was resuspended in buffer B (75 mM Tris-HCl, pH 7.5, 12.5 mM $MgCl_2$, 0.3 mM EDTA, 1 mM EGTA, 250 mM sucrose) in a concentration of 80 mg wet cell weight in 0.5 mL buffer, aliquoted and flash frozen on dry ice. Protein content was determined using the bicinchoninic acid assay in the presence of sulfhydryl reagents with bovine serum albumin (BSA) as a standard.

In binding experiments, 15 μg protein/well membrane preparation and 1 nM ketanserin hydrochloride, [ethylene-$^3$H] (PerkinElmer) as radioligand were incubated with compounds or vehicle (DMSO, 1% (v/v) final concentration) in an incubation buffer (50 mM Tris, 0.3% BSA, pH 7.4). Non-specific binding (NSB) was determined in the presence of 1 μM mianserin hydrochloride (Tocris, Bristol, UK). Samples were incubated in a final volume of 250 μL for 15 minutes at 25° C. Binding reactions were terminated by rapid filtration through a Filtermate™ harvester (PerkinElmer) using UniFilter® GF/C plates pre-soaked for at least 1 hour in 0.5% (v/v) polyethylene imine (PEI, dissolved in distilled water). The filter plates were washed three times with 0.5 mL of ice-cold washing buffer (50 mM Tris, pH 7.4). Washed filter plates were dried at 40° C. for 60 minutes and 40 μL of Microscint™-20 scintillation cocktail (PerkinElmer) was added to each well. Radioactivity was determined with a MicroBeta$^2$® microplate counter (PerkinElmer).

Non-specific binding was subtracted from raw scintillation counts to yield specific binding which was normalized to vehicle-treated samples and converted to displacement % values. $IC_{50}$ values (i.e., concentration of compound which displaces 50% of specific bound radioligand) were determined from concentration-displacement curves by sigmoidal fitting using Origin® 7.5. software (OriginLab© Corporation, Northampton, MA, USA). $K_i$ values shown in Table 11 (i.e., inhibition constants) were calculated using the Cheng-Prusoff equation: $K_i = IC_{50}/[1+([L]/K_D)]$, where [L] is the used radioligand concentration and determined by scintillation counting, and $K_D$ is the affinity of the labelled ligand for receptor, determined in a separate experiment. Competitive binding assays were performed in a minimum of six concentrations with three replicates of each concentration, in two independent experiments. The $pK_i$ values shown in Table 11 were derived by calculating the negative logarithm of the $K_i$ values expressed in mol/liter. The results indicate that the examples of the present disclosure are ligands of human recombinant 5-$HT_{2A}$ receptors.

TABLE 11

| Example | 5-$HT_{2A}$ $pK_i$ |
| --- | --- |
| 1 | 7.64 |
| 2 | 7.81 |
| Ref. Ex. 2 | 7.53 |

Characterization of Antagonism at Human 5-$HT_{2A}$ Receptors using Fluorometric $Ca^{2+}$ Detection CHO-K1 cells expressing human recombinant 5-$HT_{2A}$ receptors and $G\alpha_{16}$ (purchased from Euroscreen Fast, Brussels, BE) in culture were cryopreserved according to established protocols, using 90% FBS/10% DMSO as medium. Prior to the experiment, cells were thawed, resuspended in PowerCHO™ 2 medium (Lonza, Basel, Switzerland) supplemented with 10% fetal bovine serum (FBS), 1% penicillin-streptomycin antimycotic solution, and 1% pyruvate. Cells were seeded in 96-well microplates at a density of 40,000 cells/well and incubated overnight at 37° C. in a humidified atmosphere containing 5.0% $CO_2$. On the day of the experiment, plates were washed with assay buffer (140 mM NaCl, 5 mM KCl, 2 mM $MgCl_2$, 2 mM $CaCl_2$), 10 mM 2-[4-(2-hydroxyethyl)piperazin-1-yl]ethane-1-sulfonic acid (HEPES), 10 mM glucose, 2 mM probenecid, pH 7.4) using a plate washer (Elx405UCWS, Biotek, Winooski, VT, USA), then 50 μL/well of 4 μM Fluo-4 AM (Thermo Fisher Scientific) in assay buffer was added. After dye loading (60 minutes, 37° C., in darkness), plates were washed with assay buffer using the plate washer leaving 50 μL/well residual volume, then 50 μL/well assay buffer containing vehicle (3% DMSO in assay buffer) or test compounds (3× of the final concentration) were added and the cells were incubated for an additional 10 minutes at 37° C.

Final DMSO concentration was 1% (v/v) for all treatments. To achieve this, a series of DMSO stock solutions were prepared from all test compounds. The stock solutions were stored at −20° C. and were further diluted in assay buffer to obtain the desired final concentration immediately before the measurement. Stock solution of 5-HT (10 mM) was prepared by dissolving 5-HT in deionized, ultrafiltered water.

Baseline and agonist-evoked $[Ca^{2+}]_i$ (intracellular $Ca^{2+}$) changes were monitored with a FlexStation® II 96 well plate reader (Molecular Devices, San Jose, CA, USA). Settings for the FlexStation® II were as follows for fluorescence imaging: excitation at 485 nm; emission at 525 nm with a cutoff filter at 515 nm. Fluorescence measurements were carried out at 37° C. with a run time of 40 seconds and a sampling interval of 1.36 seconds. Excitation and detection were through the bottom of the plate. Baseline was recorded for 20 seconds followed by agonist stimulation, when 50 μL 3× concentrated agonist (5-HT at its $EC_{80}$) solution or assay buffer/vehicle was added to all wells at 75 μL/second using the onboard pipettor, at a height corresponding to 155 μL. Fluorescence was monitored for an additional 20 seconds.

Compounds were evaluated against an $EC_{80}$ 5-HT concentration, as determined on each plate with the built-in curve fitting module of the measurement software (SoftMax® Pro 5.2, Molecular Devices, San Jose, CA, USA).

Results were expressed as ΔF/F values, where F was the baseline fluorescence defined as the average fluorescence preceding and/or right after agonist administration and ΔF was the increase in fluorescence after agonist administration; calculated as $\Delta F = F_{max} - F$, where $F_{max}$ is maximal fluorescence between reads 17-29 and F is average of fluorescence reads 2-13. In all experiments, all treatments were measured in multiple wells in parallel, and the mean ΔF/F values were used for further analysis. Mean ΔF/F values were converted to inhibition % (I %) values using the following formula: I %=100×[1−((ΔF/F$_{compound}$−ΔF/F$_{vehicle}$)/(ΔF/F$_{control}$−ΔF/F$_{vehicle}$))]. IC$_{50}$ values for test compounds were determined using the SoftMax® Pro software (Molecular Devices) from 4-parameter sigmoidal concentration-effect curves fitted to the inhibition % data. Further calculation of the pIC$_{50}$ values shown in Table 12 were derived by calculating the negative logarithm of the IC$_{50}$ values, expressed as mol/liter, by the above software. The results indicate that the examples of the present disclosure are antagonists of human recombinant 5-HT$_{2A}$ receptors.

TABLE 12

| Example | 5-HT$_{2A}$ Ca$^{2+}$ pIC$_{50}$ |
| --- | --- |
| 1 | 6.80 |
| 2 | 6.88 |
| Ref. Ex. 2 | 6.75 |

Phencyclidine-Induced Hypermotility in Rats

Spontaneous locomotor activity was measured using a six-channel activity monitor manufactured by Experimetria Ltd. (Budapest, HU). The apparatus consisted of acrylic cages (48.5 cm×48.5 cm×40 cm) equipped with 2 times 30 pairs of photocells on the walls, close to the bottom of the cage to detect horizontal ambulatory behavior. Additional arrays of photocells (30 pairs) were placed along opposite sides of the cage at different heights (6.5 cm, 12 cm, 18 cm and 23 cm) in order to detect rearing responses. The signals, caused by breaking of photocell beams, were processed by motion-analyzing software (Experimetria) which determined the spatial position of the animal with 1 Hz sampling frequency, and computed the time spent by the rats ambulating.

Test compounds were administered to study animals either orally or subcutaneously, with ten animals per treatment group. In these studies, male Harlan-Wistar rats (Toxi-Coop, Budapest, HU) weighing 190-210 grams were used. After oral administration of test compound or vehicle, animals were individually habituated to the activity monitors for 30 minutes. In the cases of subcutaneous administration of test compounds, rats were first habituated for 15 minutes to the activity monitors, then treated with the test compound or vehicle followed by replacing them into the activity monitors for an additional 15-minute period of habituation. After habituation, rats were subcutaneously treated with phencyclidine hydrochloride (PCP) and replaced into the experimental apparatus immediately for the measurement period (one hour).

Data were analyzed using GraphPad® Prism® 9 software (GraphPad, San Diego, CA, USA). Statistical evaluation was performed after one hour of activity (time spent with ambulation). Drug effect was evaluated using Analysis of Variance (ANOVA, or Welch's ANOVA when appropriate) followed by Dunnett's multiple comparisons test. When appropriate, the ED$_{50}$ value was determined from percent inhibition data from linear regression analysis. ED$_{50}$ values are shown in Table 13.

TABLE 13

| Example | PCP (MED, mg/kg) | PCP (ED$_{50}$ mg/kg) |
| --- | --- | --- |
| 1 | 0.4 | 0.07 |
| Ref. Ex. 2 | 0.1 | 0.09 |

MED = minimum effective dose (the lowest dose showing statistically significant effect)

The above data (Table 13) shows that the compounds of the examples of the present disclosure showed a good and potent pharmacodynamic effect/activity in the phencyclidine-induced hypermotility in rats, indicating that they may have substantial antipsychotic efficacy.

Apomorphine-Induced Climbing and Sniffing in Mice

Male CD1® mice (Envigo, Horst, NL) weighing 24-29 g were used in the experiments (n=12 per treatment group). Climbing and sniffing behavior were measured by visual observation in cylindrical cages. The cages were 15 cm high, 12 cm in diameter, with walls of vertical metal bars, 2 mm in diameter and 1 cm apart, mounted on a smooth plastic surface.

Immediately after the subcutaneous administration of the vehicle or the test compound, animals were placed into the cages for 10 minutes to habituate. At the end of the 10-minute habituation period, 1.5 mg/kg apomorphine hydrochloride was administered subcutaneously. After treatment, animals were replaced into the cylindrical cages. The measurement of climbing and sniffing behavior started 10 minutes after the apomorphine treatment (during the 11$^{th}$ minute) and lasted for 16 minutes. Every minute the climbing behavior was scored as follows: four paws on the floor (0 score); forefeet touching the bars (1 score); and four paws grasping the bars (2 score). Animals were also rated for repetitive sniffing as a measure of stereotypy according to the following scale: no sniffing (0 score), moderate sniffing, little snout contact with cage walls or floor (1 score); and constant sniffing, persistent snout contact (2 score).

Data were analyzed using GraphPad Prism 9 software (GraphPad). Scores for both behaviors were tallied for each individual (possible maximum score 32) and group means were calculated. Drug effect was calculated as percent inhibition of the apomorphine-induced behavior. From the percentage inhibition data, dose-response curves were plotted and ED$_{50}$ values were computed by simple linear regression.

TABLE 14

| Example | APO (ED$_{50}$ cl mg/kg) | APO (ED$_{50}$ sn mg/kg) |
| --- | --- | --- |
| 1 | 0.1 | 0.4 |
| Ref. Ex. 2 | 0.27 | 0.38 |

APO cl = apomorphine-induced climbing in mice;
APO sn = apomorphine-induced sniffing in mice The above data (Table 14) shows that the compounds of the examples of the present disclosure show a good and potent pharmacodynamic effect/activity in the apomorphine-induced climbing and sniffing in mice, indicating that they may have substantial antipsychotic efficacy.

It is understood that the foregoing detailed description and accompanying examples are merely illustrative and are not to be taken as limitations upon the scope of the disclosure, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the disclosure, may be made without departing from the spirit and scope thereof. All publications, patents, and patent applications cited herein are hereby incorporated by reference in their entirety for all purposes.

We claim:

1. A compound having the structure:

2. A compound having the structure:

3. A pharmaceutically acceptable salt of a compound having the structure:

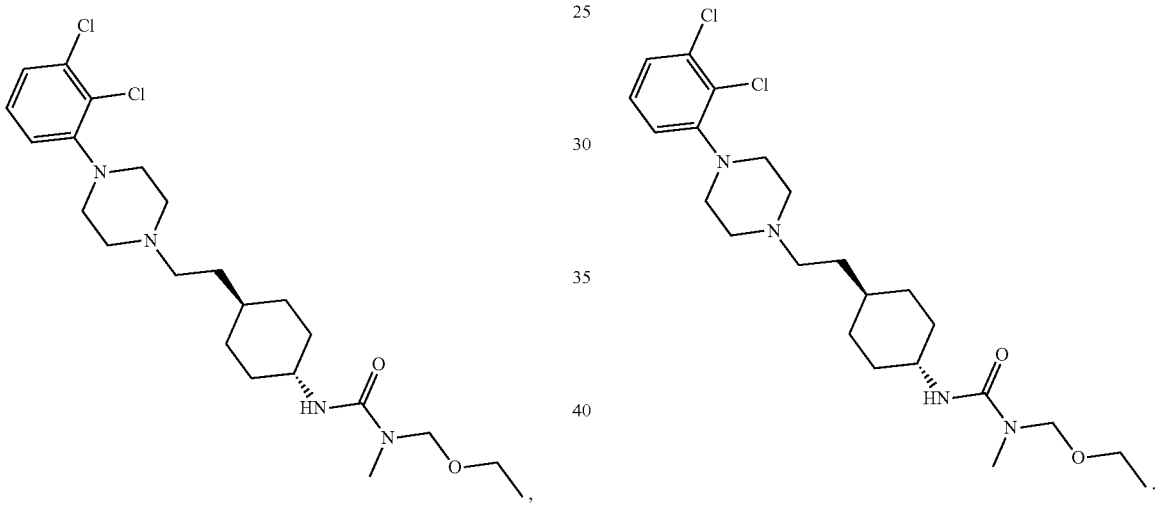

or a pharmaceutically acceptable salt thereof.

* * * * *